(12) United States Patent
Jones

(10) Patent No.: US 10,618,683 B2
(45) Date of Patent: Apr. 14, 2020

(54) LOCKABLE PACKAGING

(71) Applicant: WestRock MWV, LLC, Norcross, GA (US)

(72) Inventor: Marty Jones, Glen Allen, VA (US)

(73) Assignee: WestRock MWV, LLC, Atlanta, GA (US)

( * ) Notice: Subject to any disclaimer, the term of this patent is extended or adjusted under 35 U.S.C. 154(b) by 0 days.

(21) Appl. No.: 15/556,729

(22) PCT Filed: Feb. 23, 2016

(86) PCT No.: PCT/US2016/019013
§ 371 (c)(1),
(2) Date: Sep. 8, 2017

(87) PCT Pub. No.: WO2016/144524
PCT Pub. Date: Sep. 15, 2016

(65) Prior Publication Data
US 2018/0105314 A1    Apr. 19, 2018

Related U.S. Application Data

(60) Provisional application No. 62/130,182, filed on Mar. 9, 2015.

(51) Int. Cl.
| | | |
|---|---|---|
| *B65D 5/38* | (2006.01) | |
| *A61M 5/00* | (2006.01) | |
| *A61J 1/16* | (2006.01) | |
| *B65D 5/10* | (2006.01) | |
| *B65D 5/42* | (2006.01) | |

(52) U.S. Cl.
CPC .............. *B65D 5/38* (2013.01); *A61J 1/16* (2013.01); *A61M 5/002* (2013.01); *B65D 5/106* (2013.01); *B65D 5/4266* (2013.01)

(58) Field of Classification Search
CPC ........ B65D 5/38; B65D 5/106; B65D 5/4266; A61M 5/002; A61J 1/16
USPC ................................................. 206/538, 468
See application file for complete search history.

(56) References Cited

U.S. PATENT DOCUMENTS

| | | | | |
|---|---|---|---|---|
| 7,845,496 B2 * | 12/2010 | Hession | .................... | B65D 5/38 206/528 |
| 8,100,262 B2 * | 1/2012 | Jones | ................. | B65D 83/0463 206/468 |
| 9,452,877 B2 * | 9/2016 | Grosskopf | ......... | B65D 83/0463 |
| 2007/0054525 A1 | 3/2007 | Jones | | |

(Continued)

FOREIGN PATENT DOCUMENTS

| | | |
|---|---|---|
| WO | WO 2006/088979 A1 | 8/2006 |
| WO | WO 2011/099034 A2 | 8/2011 |

*Primary Examiner* — Steven A. Reynolds
(74) *Attorney, Agent, or Firm* — WestRock IP Legal

(57) ABSTRACT

A package (90) includes an outer sleeve (60) and a drawer (50) that is slidably receivable in the outer sleeve (60). The package further includes a two-part locking mechanism for releasably locking the drawer within the outer sleeve. The first part is provided by the outer sleeve, and the second part by the drawer as a locking flap (52) hingedly connected to a rear end of a top panel (106) of the drawer (50). The locking flap is folded outwardly of the drawer toward a forward end of the top panel to be releasably engaged with the first part of the locking mechanism.

9 Claims, 5 Drawing Sheets

(56) References Cited

U.S. PATENT DOCUMENTS

| | | | |
|---|---|---|---|
| 2009/0301924 A1* | 12/2009 | Rondeau | B65D 83/0463 206/531 |
| 2011/0163156 A1* | 7/2011 | Smith | B65D 83/0463 229/125.125 |
| 2013/0140201 A1* | 6/2013 | Ghini | B65D 5/38 206/267 |
| 2015/0048001 A1 | 2/2015 | Bailey | |

* cited by examiner

LOCKABLE PACKAGING

REFERENCE TO RELATED APPLICATION

This application claims the benefit of priority under 35 U.S.C. § 119(e) of U.S. provisional application Ser. No. 62/130,182 filed on Mar. 9, 2015 which is hereby incorporated by reference in its entirety.

FIELD OF THE INVENTION

The present invention relates generally to packaging, specifically but not exclusively, to lockable packaging such as child-resistant, senior-friendly packages for healthcare type applications and optionally packaging such as sleeve-and-drawer style packages for consumer goods such as food, recreational drugs (e.g., tobaccos, cigars, cigarettes, etc.), toys, hardware, and electrical items, or the like. More specifically, but not exclusively, the invention relates to a sleeve-and-drawer style package having an internal slidable receptacle, that is releasably lockable within an outer sleeve and having a release mechanism comprising a moveable unlocking push tab or a deformable unlocking pressing area.

Typical examples of sleeve-and-drawer packages where the present invention may be employed include, but are not limited to: a secondary packages for injectables (e.g., those packages for syringes and vials); unit dose packages for pharmaceutical tablets; capsules; lozenges; and security packages to deter package pilferage for small high-value items, such as consumer electronics.

BACKGROUND OF THE INVENTION

In the field of packaging, particularly in the field of healthcare and medication packaging and in the field of sleeve-and-drawer style packaging for a wide range of consumer goods, it is often required to provide consumers or patients with secure packaging that has child-resistant features to restrict or prevent access to the package contents by a child. Many packages are available that comprise an inner drawer that holds articles in trays. The drawer typically is slidably received in an outer sleeve. The inner drawer, when fully received in the outer sleeve, is usually retained and locked inside the outer sleeve by a locking flap of the drawer that engages the outer sleeve. Such a locking flap is folded more than 90 degrees toward the open end of the outer sleeve to engage the outer sleeve and to resist withdrawing force applied by a user to the inner drawer. For the purpose of providing a proper resistance or stiffness to such withdrawing force, the size or length of the locking flap plays an important role. The length of the locking flap substantially affects its stiffness. The length of the locking flap also directly affects the length of the entire package. For that reason, there are needs for lockable packages that are not oversized and still provide an acceptable child-resistant feature.

The present invention seeks to provide an improvement in the field of packaging, more specifically, but not exclusively, in the field of sleeve-and-drawer style packages.

SUMMARY

According to an aspect of the invention for which protection is sought, there is provided a package including an outer sleeve and a drawer. The drawer is slidably receivable in the outer sleeve. The package further includes a two-part locking mechanism for releasably locking the drawer within the outer sleeve. The two-part locking mechanism includes a first part and a second part. The first part is provided by the outer sleeve. The drawer includes a top panel and a base panel hingedly connected together by a pair of side panels to provide a tubular structure. The rear end of the top panel is disposed proximate a closed end of the outer sleeve when the drawer is fully received in the outer sleeve. The drawer further includes the second part of the two-part locking mechanism. The second part is a locking flap hingedly connected to the rear end of the top panel. The locking flap is folded outwardly of the tubular structure toward a forward end of the top panel to be releasably engaged with the first part of the locking mechanism.

BRIEF DESCRIPTION OF THE DRAWINGS

Embodiments of the invention will now be described, by way of example only and with reference to the following drawings.

DETAILED DESCRIPTION OF THE PREFERRED EMBODIMENTS

Figure 1:
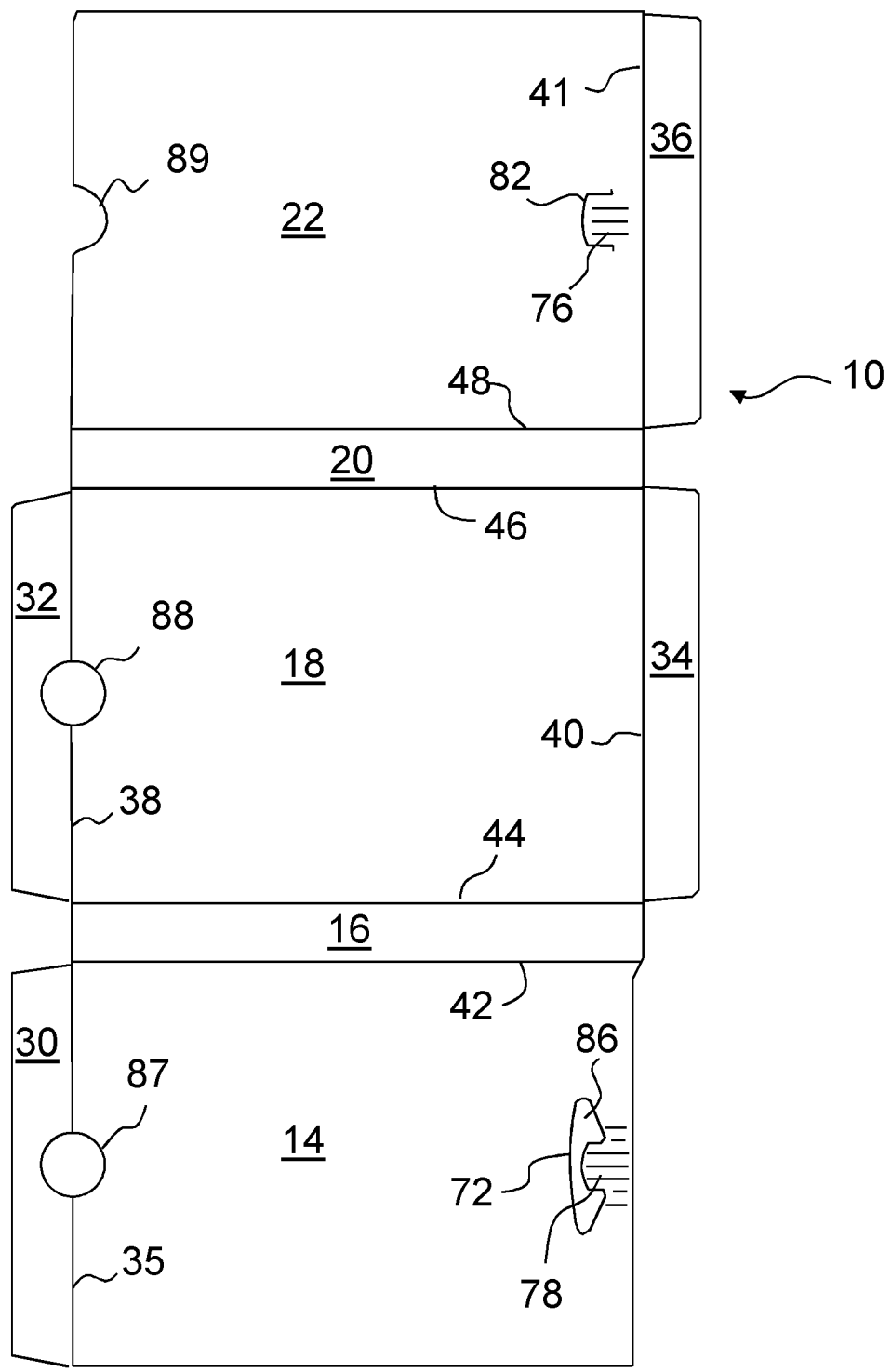
FIG. 1 is a plan view of a blank for forming an outer sleeve of a package according to the invention.

Detailed descriptions of a specific embodiment of the outer sleeve, lockable receptacle (drawer), package and blanks are disclosed herein. It will be understood that the disclosed embodiment is merely an example of the way in which certain aspects of the invention can be implemented and does not represent an exhaustive list of all of the ways the invention may be embodied. Indeed, it will be understood that the outer sleeve, lockable receptacle, package and blanks described herein may be embodied in various and alternative forms. The figures are not necessarily to scale and some features may be exaggerated or minimised to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Reference is now made to the accompanying Figures for the purpose of describing, in detail, a preferred and exemplary embodiment of the invention. The figures and detailed description are provided to describe and illustrate examples in which the disclosed package and its parts may be made and used, and are not intended to limit the scope thereof. Those skilled in the art will readily appreciate that the disclosed packages can be used to store a variety of products. More specifically, the disclosed lockable receptacle can be used for the storage of products, such as for example, syringes, medication and other medical or pharmaceutical products, smokeless tobacco, cigarettes, confectionary, tea bags, mints, electrical items or any product stored in a pouch, blister or compartment, and the like without departing from the inventive aspects of the present invention.

Generally the present invention teaches the provision of a locking flap for use with a variety of lockable packages wherein a locking flap is required to be released, out of its locked position by means of a releasing mechanism. The releasing mechanism is provided on an outer sleeve of the package. Such a package is typically utilized in applications where child-resistance is required (for example in pharmaceutical and healthcare packaging), however the application of the locking flap is not so limited and its application in other forms of packaging, such as high-value product secure packaging and repeated use packaging is envisaged. The drawer and locking flap of the invention may be utilized with a variety of styles of lockable package, made from a variety of materials, including for example, plastics material, paperboard and combinations thereof. The locking flap is typically made out of material forming the main part of the drawer or inner receptacle and hingedly connected by a fold line to the drawer; however, it optionally may be formed from a separate piece of material and affixed to the main part of the drawer. The locking flap is connected to an upper panel of a holding structure of the drawer.

A specific embodiment of the invention is illustrated herein in relation to a sleeve and drawer style package (formed primarily of paperboard), wherein a lockable drawer 50 (optionally formed from sheet plastic or composite paperboard material) retained within the outer sleeve 60 holds plurality of packaged syringes 54 (only one shown in FIG. 4) and one vial 55. It is to be understood however, that the locking flap, drawer and package of the invention is not limited to this particular application.

Figure 2:
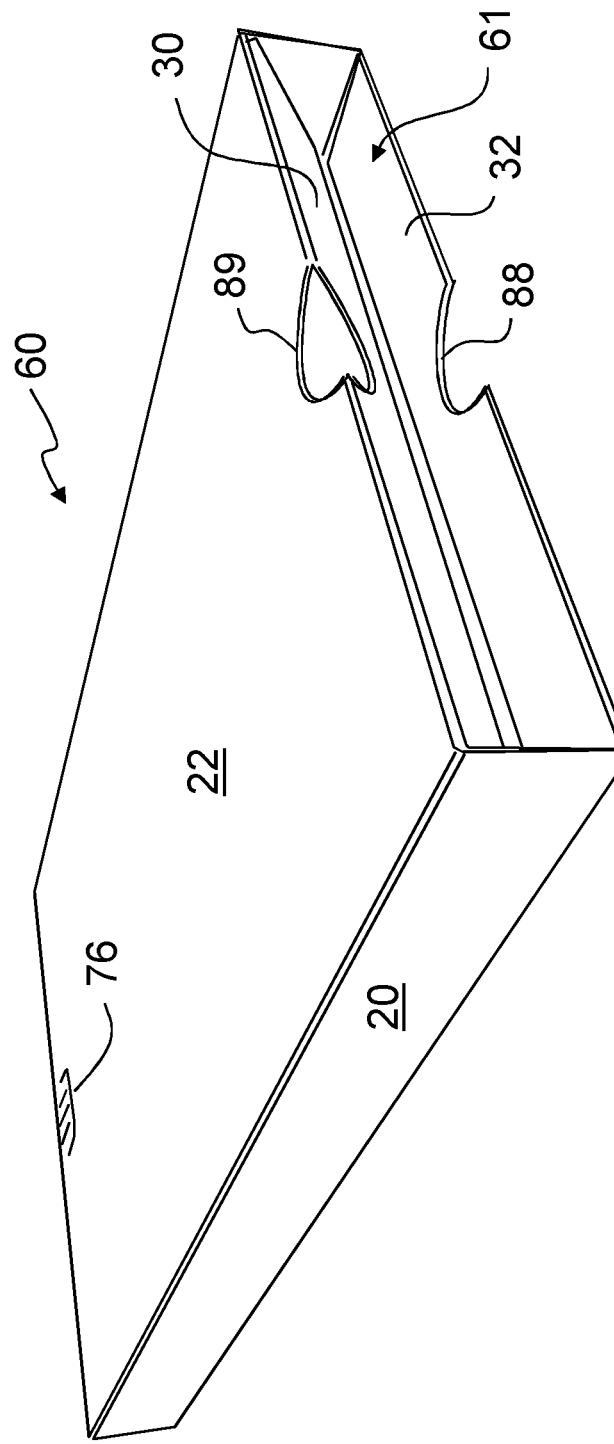
FIG. 2 is a perspective view of the outer sleeve formed from the blank of FIG. 1.
Figure 3:
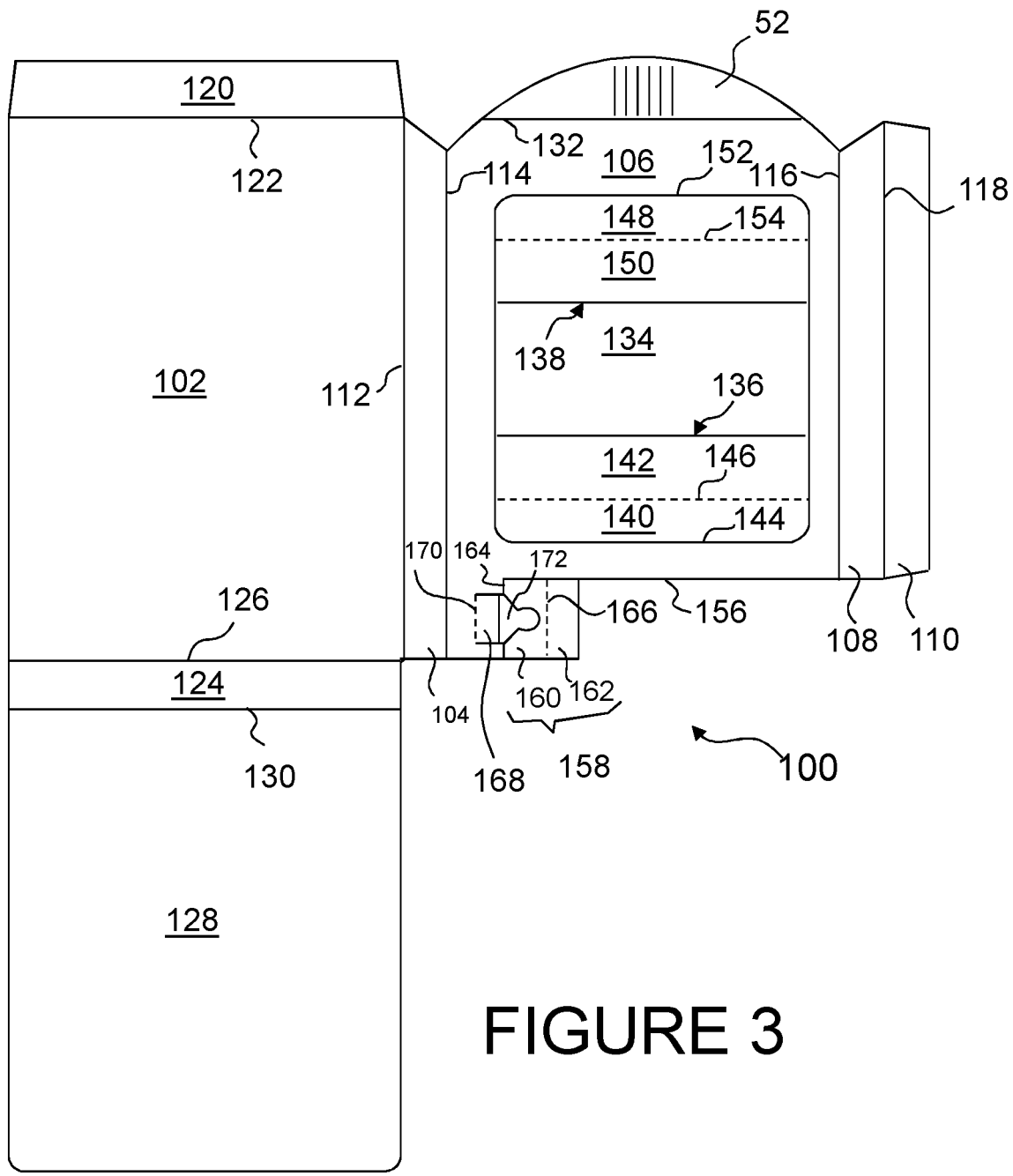
FIG. 3 is a plan view of an inner receptacle or drawer of the package according to the invention.
Figure 4:
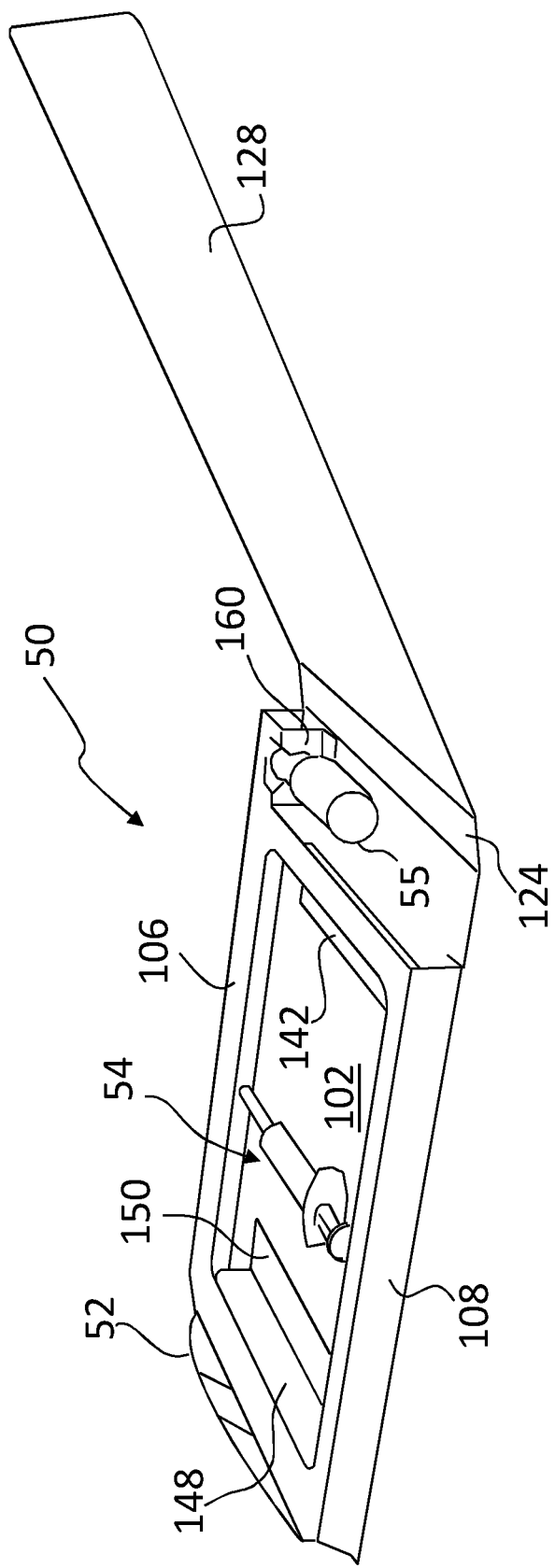
FIG. 4 is a perspective view of the drawer formed from the blank of FIG. 3, showing a cover panel of the drawer in its opened position.
Figure 5:
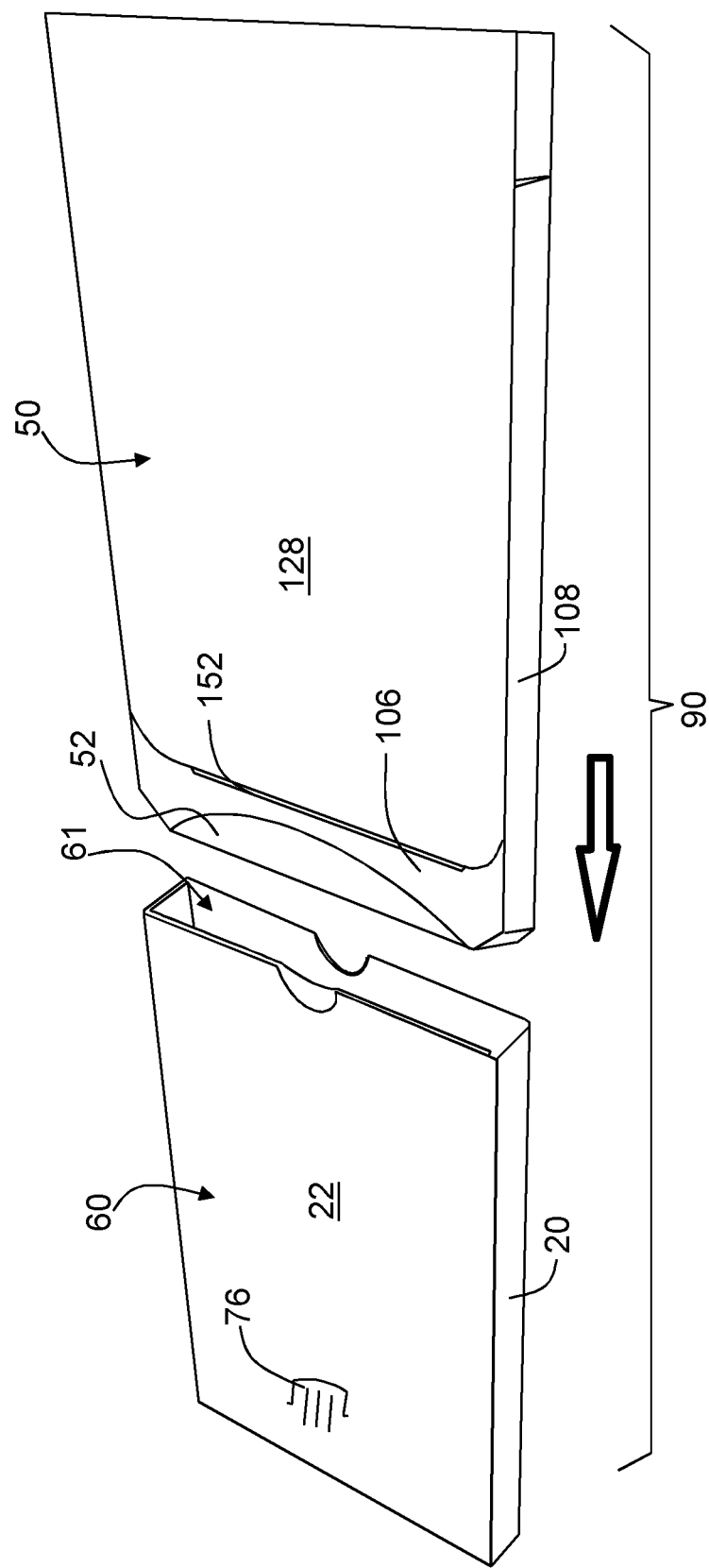
FIG. 5 is a perspective view of the outer sleeve and drawer, showing a condition before the drawer is inserted into the outer sleeve.

Referring now to FIG. 1 through to 5, there is illustrated a package 90 and component parts thereof according to an embodiment of the invention. FIG. 5 is a perspective view of a package 90 wherein the two parts 50, 60 of the package is separated from each other. The package 90 is a sleeve-and-drawer style package comprising an outer sleeve 60 formed from a blank 10 (see FIG. 1) and a lockable drawer 50 formed from a blank 100 (see FIG. 3). The lockable drawer 50 in an erected form is shown in FIG. 4 and is of the form of a tray with an integrally formed cover panel 128. The outer sleeve 60 comprises a first part of a two-part complementary locking mechanism. In this embodiment, the first part of the two-part complementary locking mechanism comprises a 1-ply locking edge 72 (see FIG. 1). The drawer 50 comprises a second part of the two-part complementary locking mechanism. In this embodiment, the second part of the two-part complementary locking mechanism comprises a locking flap 52 (see FIG. 4). The package 90 also comprises a release mechanism which is, in this arrangement, entirely formed in the outer sleeve 60. The release mechanism comprises an outer moveable tab 76 (see FIGS. 1 and 2) and an associated, optional inner moveable tab 78 (see FIG. 1).

The drawer 50 is slidably insertable into the interior cavity of the outer sleeve 60 through an open end 61 of the outer sleeve 60 (see FIG. 5) and is releasably locked therein by operation of the two-part complementary locking mechanism.

Referring now to FIG. 1, the blank 10 illustrated therein is formed of a foldable substrate or sheet material, for example, paperboard, optionally having at least one coated and printed side. In other embodiments, the blank may be formed from any one or a combination of: paper, paperboard, fibreboard, plastics material, coated material (e.g., tear-resistant coated material), uncoated material and printed material. Optionally in the present embodiment, the blank 10 is a sheet of paperboard.

The blank 10 comprises, in series: an outer top panel 22 (also referred to herein as a first top panel), a first side panel 20, a bottom panel 18, a second side panel 16, and an inner top panel 14, hinged one to the next by means of longitudinally extending hinged connections such as fold lines 48, 46, 44 and 42 respectively.

Rear end flaps 34, 36 are hinged by hinged connections such as fold lines 40, 41 to the "rear"-ends of the bottom panel 18 and outer top panel 22. These rear end flaps 34, 36, in use are folded approximately 90° about fold lines 40, 41 and are affixed in face contacting relationship to one another to form a composite end wall 34/36 for the outer sleeve 60. The composite end wall 34/36 may be referred to herein as a "rear" end wall.

Optional end flaps 32 and 30 are hinged by hinged connections such as fold lines 38 and 35 to the "open"-ends of the bottom panel 18 and inner top panel 14 respectively. These end flaps 32, 30, in use are folded approximately 180° about fold lines 38 and 35 and are affixed in face contacting relationship to the bottom panel 18 and to the inner top panel 14 respectively. Once affixed in this way, the end flaps 32, 30 optionally serve to provide a smooth finish to the "open" end of the outer sleeve 60 and serve to prevent or at least mitigate against the complete withdrawal of the lockable drawer 50 from the outer sleeve 60. In an alternative embodiment, however, the end flaps 32, 30 may be folded substantially more than 90° and less than 180° and remain unattached to the bottom panel 18 or inner top panel. Those unattached front end panels can also serve to prevent or at least mitigate against the complete withdrawal of the lockable drawer 50 from the outer sleeve 60.

The blank 10 comprises elements for forming the first part of the two-part locking mechanism. The elements include: a first aperture 86 and a first edge 72 formed in the inner top panel 14 (the first edge 72 optionally being defined by the aperture 86). Once assembled into the outer sleeve 60, the first edge 72 provides a one-ply engaging edge 72.

The blank 10 further comprises elements for forming the release mechanism when in an assembled form in the outer sleeve 60. The elements for forming the release mechanism include: an outer moveable tab 76 formed in the outer top panel 22; an inner moveable tab 78 formed in the inner top panel 14. Each moveable tab 76, 78 is preferably, but nevertheless optionally integrally formed within the blank 10. Each moveable tab 76, 78 comprises an anchored portion and a free edge which is defined by a cut, severance line or opening such that the free edge is separated, or otherwise separable, from the remainder of the respective one of the outer top panel 22 and inner top panel 14. The moveable tabs 76, 78 are thereby moveable below the plane of the panels 22, 14 from which they are formed. Optionally, the outer moveable tab 76 formed in the outer top panel 22 has larger size than the inner moveable tab 78 in the inner top panel 14.

The outer moveable tab 76 may be defined by a generally "U" shaped severance line 82 such as a perforation or cut. The inner moveable tab 78 may be defined in part by the aperture 86 forming the locking edge 72. The aperture 86 may be considered as recesses into which the locking flap 52 may be inserted when the flap 52 is in the locked position. The roughly "U"-shaped moveable tab 76 is preferably, but nevertheless optionally, disposed in a substantially medial position within the outer top panel 22.

Turning in more detail to the construction of the outer sleeve, from the blank 10; optionally, end flaps 32, 30 are folded about fold lines 38, 35 and affixed (or optionally not affixed) to the inside faces (non-printed faces) of the bottom panel 18 and the inner top panel 14 respectively. To affix the end flaps 32, 30 to the bottom panel 18 and to the inner top panel 14, adhesive (such as hot melt glue) may be applied to one or both of the end flap 32 and the bottom panel 18; and to one or both of the end flap 30 and the inner top panel 14. After folding the end flaps 32, 30, the inner top panel 14 is folded over the bottom panel 18 about the fold line 42. Then, the outer top panel 22 is folded over the inner top panel 14 about the fold line 46. Adhesive or other affixing means may be used to securely affix the outer top panel 22 to the inner top panel 14. The end flaps 32, 30 provide folded edges of the front open end of the outer sleeve 60 and one or both may additionally serve as a stopper to prevent or at least restrict the complete withdrawal of a lockable drawer 50 from the outer sleeve 60.

The (non-printed surface of the) outer top panel 22 is in part affixed to the (printed surface of the) inner top panel 14. This may be achieved by the application of adhesive (such as a hot melt glue) to the outer top panel 22 and/or to the inner top panel 14. At this point, construction of the outer sleeve 60 is not entirely completed since the rear end wall 34/36 has not been assembled. In this state, however, the outer sleeve 60 is in its flat-form (not shown). It has been folded and part assembled and it is in this flat-form that the outer sleeve 60 would preferably be shipped. As such, construction of the outer sleeve 60 may be fully completed at a packaging plant, where the outer sleeve 60 is opened into a tubular form with an interior cavity and loaded with the lockable drawer 50 through one or both of the open (front) or rear ends of the outer sleeve 60. Then, the rear end wall 34/36 is constructed by folding the rear end panels 34, 36 about fold lines 40, 41 and into affixed and face contacting relationship.

The lockable drawer 50 may also be formed from foldable sheet material such as paperboard, sheet plastic, a paperplastic composite material. FIG. 3 illustrates a blank 100 from which the lockable drawer 50 is formed. The blank 100 comprises a tray base panel 102, a first tray side panel 104, an tray top panel 106, a second tray side panel 108 and a glue flap 110, which are hingedly connected, one to the next, by hinged connections such as fold lines 112, 114, 116, and 116 respectively. A rear end closure panel 120 is hingedly connected to the rear end of the tray base panel 102 along a hinged connection such as a fold line 122. A spine panel 124 is hingedly connected to the front end of the tray base panel 102 along a hinged connection such as a fold line 126. A cover panel 128 is hingedly connected to the spine panel 124 along a hinged connection such as a fold line 130. The locking flap 52 is hingedly connected to the rear end of the tray top panel 106 along a hinged connection such as a fold line 132.

The tray base panel 102 and tray top panel 106 may be considered major panels each having a substantially larger area than either of the first tray side panel 104 and second tray side panel 108 which may be considered minor panels.

The tray top panel 106 is provided with a generally rectangular top opening 134. The material struck from the tray top panel 106 to define the top opening 134 is used in part to provide a front interior member 136 and in part to provide a rear interior member 138. The front interior member 136 comprises a tray front panel 140 and a front foot panel 142. The tray front panel 140 is hingedly connected to the front edge of the top opening 134 along a hinged connection such as a front fold line 144. The front foot panel 142 is hingedly connected to the tray front panel 140 along a hinged connection such as a fold line 146. The rear interior member 138 comprises a tray rear panel 148 and a rear foot panel 150. The tray rear panel 148 is hingedly connected to the rear edge of the top opening 134 along a hinged connection such as a fold line 152 while the rear foot panel 150 is hingedly connected to the tray rear panel 148 along a hinged connection such as a fold line 154. The tray front and rear panels 140, 148 respectively provide substantial front and rear end walls of the drawer 50. The tray front and rear panels 140, 148 define therebetween a first article-receiving space immediately below the top opening 134 when the blank 100 is assembled into the tray-shaped drawer 50.

Along the forward end edge of the tray top panel 106, a cutout 156 is defined to provide a second article-receiving space. The material struck from the tray top panel 106 to define the cutout 156 is partially used to provide a side interior member 158. The side interior member 158 comprises a first inner side panel 160 and a side foot panel 162. The first inner side panel 160 is hingedly connected to the tray top panel 106 along a hinged connection such as an interrupted fold line 164. The side foot panel 162 is hingedly connected to the first inner side panel 160 along a hinged connection such as a fold line 166. The first inner side panel 160 is provided with a neck-receiving recess 172. In addition, a second inner side panel 168 is struck from the tray top panel 106 at the area next to the cutout 156 to define a cap-receiving area. The second inner side panel 168 is hinedly connected to the tray top panel 106 along a hinged connection such as a fold line 170. The first and second inner side panels 160, 168 provide a double end wall which defines an end of the second article-receiving space.

Turning to the construction of the drawer 50 from the blank 100; optionally, the rear end closure flap 120 is folded over the inside surface of the tray base panel 102 about the fold line 122. When the drawer is erected, the end closure panel 120 may take an end closing position wherein the end closure panel 120 defines an acute angle with respect to the tray base panel 102. To retain the end closure panel 120 in the closing position, the end closure panel 120 has a height greater than each of the tray side panels 104, 108, which will be discussed in more details later. After the end closure flap 120 is folded, the glue flap 110 is folded over the second tray side panel 108 about the fold line 118. Then the tray top panel 106 is folded over the inside/upper surface of the tray base panel 102 about the fold line 114. Glue or any other adhesive is applied to the glue flap 110 and the side foot panel 162 to secure the glue panel 110 and the side foot panel 162 to the inside surface of the tray base panel 102. The glue or any other adhesive may alternatively be applied to the tray base panel 102 or to all of the tray base panel 102, the glue panel 110 and the side foot panel 162.

At this point, the construction of the drawer 50 is not entirely completed since the locking flap 52 is not folded about the fold line 132 and none of the front, rear and side interior members 136, 138, 158 has been erected. In this state, however, the drawer 50 is in its flat-form (not shown). It has been folded and part assembled and it is in this flat-form that the drawer 50 would preferably be shipped. As such, construction of the drawer 50 may be fully completed at a packaging plant, where the drawer 50 is opened to form a tubular structure, and the front and rear interior members 136, 138 are folded inwardly of the tubular structure to define the first article-receiving space below the top opening 134. The tray front and rear panels 140, 148 are folded downward about the fold lines 144, 152 to take respective upright positions while the front and rear foot panels 142, 150 are folded about the fold lines 146, 154 to be in flat face contacting positions with respect to the inside/upper surface of the tray base panel 102. The side interior member 158 is automatically erected when the drawer 50 takes the tubular form due to the side foot panel 162 that has been secured to the tray base panel 102. When erected, the first inner side panel 160 automatically takes an upright position while the second inner side panel 168 remains in the plane of the tray top panel 106 till it is manipulated later. During the drawer-erecting process, the end closure panel 120 is somewhat folded backward/upward about the fold line 122 due to the natural resiliency of the sheet material. This allows the end closure panel 120 to take the end-closing position wherein the upper end of the end closure panel 120 is in abutment with the inside/lower surface of the tray top panel 106 and thereby prevents the end closure panel 120 from folded further backwards. This glue-free end closure panel 120 can thereby be retained in its end-closing position. Stated differently, the height of the end closure panel 120 is greater than the height of the tubular structure. The tubular structure is then loaded with any articles such as syringes and vials through the top opening 134 and the cutout 156. For example, packaged syringes 54 are placed inside the first article-receiving space while a vial 55 is received in the second article-receiving space (see FIG. 4). More specifically, the cap of the vial 55 is pressed into the cap-receiving area defined by the second inner side panel 168, till the neck of the vial 55 snaps in the neck-receiving recess 172. The syringes 54 are simply loaded into the space between the tray front and rear panels 140, 148. After that, the spine panel 124 is folded about the fold line 126 to take an upright position where it closes the front end of the second article-receiving space. Then, the cover panel 128 is folded about the fold lines 130 over the tray top panel 106 to cover the top opening 134. The locking flap 52 is finally folded toward the top opening 134 so that the drawer 50 is ready to be loaded into the outer sleeve 60.

Referring to FIG. 5, the lockable drawer 50 moved in the direction of the arrow and thereby is inserted with its rear end first into the outer sleeve 60. When fully inserted, the drawer 50 is automatically locked in the sleeve 60 by operation of the two-part complementary locking mechanism. The drawer 50 is loaded into the sleeve 60 such that the tray base panel 102 is in a face contacting arrangement with the inside surface of the bottom panel 108 and that the folded locking flap 52 is in a sliding contact at its upper end with the inside surface of the inner top panel 14. When the drawer 50 is fully received in the outer sleeve 60, the folded locking flap 52, due to its natural resilience, unfolds slightly into the recess provided by the aperture 86. In this way, the locking flap 52 catches on the locking edge 72 provided by the inner top panel 14.

To allow the drawer 50 to be unlocked and thereby to enable it to be slidable with respect to the outer sleeve 60, the releasing mechanism needs to be activated. The releasing mechanism comprises the moveable tabs 76, 78 which are disposed in registry with each other when the sleeve 60 is in its assembled form. Activation of the release mechanism may be achieved by depressing the outer moveable tab 76, which in turn causes depression of the inner moveable tab 78. Depressing the release mechanism sufficiently depresses the locking flap 52 such that it is no longer in locking engagement with the locking edge 72. Simultaneously, the lockable drawer 50 can be withdrawn from the outer sleeve 60. Thumb recesses 87, 88, 89 may assist a user in grasping the lockable receptacle 50, when it is disposed fully within the outer sleeve 60, in order to withdraw it from the outer sleeve 60. As such it will be realized that a user is required to hold the package 90 in one hand and with that same hand, depress the moveable tab 76 whilst, at the same time, gripping and pulling a forward end of the lockable drawer 50 with their other hand.

In the assembled form, the tray top panel 106 is disposed above the tray base panel 102 as best shown in FIG. 4. When such a drawer 50 is received in the outer sleeve, the tray top panel 106 disposed at the position immediately below the inner top panel 14 of the outer sleeve 60. Under such circumstances, connecting the locking flap 52 to the tray top panel 106 is advantageous in that:

the locking flap 52 is allowed to be short and stiff and yet can reach the locking edge 72;

the short locking flap 52 may allow the entire length of the package 90 to be reduced to save the amount of the material used to form the package; and users of the package can operate the releasing mechanism while viewing the tab 76 and at the same time the drawer 50 may be withdrawn with its top opening 134 facing up—in this way, the chance of the articles 54, 55 accidentally falling out of the drawer 50 may be reduced.

It can be appreciated that various changes may be made within the scope of the present invention, for example, the size, number, configuration, position and relative placement, shape and physical formation of each panel, the locking mechanism and the moveable tabs of the releasing mechanism may be adjusted to suit the locking mechanism and/or size and/or color and/or design and/or intended purpose of the package.

Optionally, it is additionally envisaged that the moveable tab 76 may be replaced by a demarcated, deformable pressing zone provided in an outer top panel of the package. Such a pressing zone of the outermost panel may be in registry with the underlying moveable tab 78 or otherwise the underlying aperture 86. The pressing zone is nevertheless caused to be depressed sufficiently to cause the unlocking of the locking flap 52

In the embodiments comprising a pressing region or zone, the pressing zone may be a demarcated pressing zone and may comprise any one or more of: an embossment, debossment, crease, groove, compressed region of material, integrally formed raised button or recess. Optionally the demarcated region may be formed by any one or more or an appropriate combination of: thermo-forming, molded, blow-molded, pressed, grooved, engraved, scored, and hatched.

It will be recognised that as used herein, directional references such as "top", "bottom", "base", "front", "back", "end", "side", "inner", "outer", "upper" and "lower" do not necessarily limit the respective panels to such orientation, but merely serve to distinguish these panels from one another. Any reference to hinged connection should not be construed as necessarily referring to a single fold line only; indeed it is envisaged that hinged connection can be formed from one or more of the following, a short slit, a frangible line or a fold line without departing from the scope of the invention.

As used herein, the terms "hinged connection" and "fold line" each refers to all manner of lines that define hinge features of the blank or substrate of sheet material, facilitate folding portions of the blank or substrate of sheet material with respect to one another, or otherwise indicate optimal panel folding locations for the blank or substrate of sheet material. Any reference to "hinged connection" should not be construed as necessarily referring to a single fold line only; indeed a hinged connection can be formed from one or more fold lines.

As used herein, the term "fold line" may refer to one of the following: a scored line, an embossed line, a debossed line, a line of perforations, a line of short slits, a line of half-cuts, a single half-cut, an interrupted cut line, aligned slits, a line of short scores and any combination of the aforementioned options, without departing from the scope of the invention.

As used herein, the term "severance line" may refer to all manner of lines formed in the blank or substrate of sheet material that facilitate separating portions of the blank or substrate of sheet material from one another, or otherwise that indicate optimal separation locations on the blank or substrate. As used herein, the term "severance line" may refer to one of the following: a single cut line, a single partial-depth cut line (e.g., a single half-cut line), an interrupted cut line, a score line, an interrupted score line, a line of perforations, a line of short cuts, a line of short slits, a line of short partial-depth cuts (e.g., a line of short half cuts), and any combination of the aforementioned options.

It should be understood that hinged connections, fold lines and severance lines can each include elements that are formed in the blank or substrate of sheet material, including perforations, a line of perforations, a line of short slits, a line of half-cuts, a single half-cut, a cut line, an interrupted cut line, slits, scores, any combination thereof, and the like. The elements can be dimensioned and arranged to provide the desired functionality. For example, a line of perforations can be dimensioned or designed with degrees of weakness to define a fold line and/or a severance line. The line of perforations can be designed to facilitate folding and resist breaking to provide a fold line, to facilitate folding and facilitate breaking with more effort to provide a frangible fold line, or to facilitate breaking with little effort to provide a severance line.

The phrase "in registry with" as used herein refers to alignment of two or more elements in an erected package, such as a moveable tab formed in an outer top panel and a moveable tab formed in an inner top panel. Those elements in registry with each other may be aligned with each other in the direction of the thickness of the overlapping panels.

The invention claimed is:

1. A package comprising an outer sleeve and a drawer that is slidably receivable in the outer sleeve, the outer sleeve having a closed rear end and an open front end through which the drawer is insertable and withdrawable, the package further comprising a two-part locking mechanism for releasably locking the drawer within the outer sleeve, the two-part locking mechanism comprising a first part and a second part, the first part being provided by a top panel of the outer sleeve, the drawer comprising a top panel and a base panel hingedly connected together by a pair of side panels to provide a tubular structure, the top panel of the drawer being disposed adjacent to the top panel of the outer sleeve when the drawer is fully received in the outer sleeve such that the top panel of the drawer is disposed between the top panel of the outer sleeve and the base panel, the top panel of the drawer having forward and rear opposed ends, the rear end being disposed proximate the closed end of the outer sleeve when the drawer is fully received in the outer sleeve, the drawer further comprising the second part of the two-part locking mechanism, the second part comprising a locking flap hingedly connected to the rear end of the top panel of the drawer, the locking flap being hingedly attached to the top panel along a fold line extending between the locking flap and the top panel, the locking flap being folded in a direction away from an interior of the tubular structure toward the forward end of the top panel of the drawer to be releasably engaged with the first part of the locking mechanism when the drawer is fully received in the outer sleeve, further comprising an end closure panel hingedly attached to a rear end of the base panel along a fold line, wherein the tubular structure has a height between the base panel and the top panel of the drawer, and the end closure panel extends away from said fold line a distance greater than the height of the tubular structure.

2. The package of claim 1 further comprising a releasing mechanism which is formed in the outer sleeve, the releasing mechanism comprising an outer moveable tab defined in the top panel of the outer sleeve.

3. The package of claim 1, wherein the top panel of the drawer is a major panel.

4. The package of claim 1, wherein the locking flap is made of the same piece of material forming the top panel of the drawer.

5. The package of claim 1, wherein the end closure panel is a glue-free panel.

6. The package of claim 1, wherein an upper end of the end closure panel is in abutment with the inside lower surface of the top panel of the drawer.

7. The package of claim 1, wherein the end closure panel defines an acute angle with respect to the base panel.

8. The package of claim 1, wherein the height between the base panel and the top panel of the drawer is sufficient to receive a hypodermic syringe.

9. The package of claim 1, wherein the height between the base panel and the top panel of the drawer is sufficient to receive a medicine vial.

* * * * *